US007793358B2

(12) United States Patent
Frye

(10) Patent No.: US 7,793,358 B2
(45) **Date of Patent: *Sep. 14, 2010**

(54) COMFORT BRA LINER

(76) Inventor: Donna J. Frye, 26491 Merienda #1, Laguna Hills, CA (US) 92656

( * ) Notice: Subject to any disclaimer, the term of this patent is extended or adjusted under 35 U.S.C. 154(b) by 0 days.

This patent is subject to a terminal disclaimer.

(21) Appl. No.: 12/366,132

(22) Filed: Feb. 5, 2009

(65) Prior Publication Data

US 2010/0105286 A1 Apr. 29, 2010

Related U.S. Application Data

(63) Continuation-in-part of application No. 12/257,975, filed on Oct. 24, 2008.

(51) Int. Cl.
*A41D 27/12* (2006.01)
*A41C 3/00* (2006.01)

(52) U.S. Cl. .............................. 2/54; 2/55; 2/56; 2/46; 450/37

(58) Field of Classification Search ..................... 2/267, 2/268, 50, 60, 46, 53, 56, 57, 463, 465; 450/36, 450/37, 54–58, 1, 81
See application file for complete search history.

(56) References Cited

U.S. PATENT DOCUMENTS 2,534,721 A * 12/1950 Marshall ...................... 450/36
2,641,763 A 6/1953 Schroeder
2,863,460 A * 12/1958 Monroe ....................... 450/11
2,869,552 A * 1/1959 Smith .......................... 450/32
5,573,441 A * 11/1996 Smith .......................... 450/89
5,980,359 A * 11/1999 Brown ......................... 450/57
5,996,120 A 12/1999 Balit
6,203,399 B1 * 3/2001 Hackney ........................ 450/1
6,264,530 B1 * 7/2001 Cosentino .................... 450/57
7,201,629 B2 * 4/2007 Lambru ......................... 450/1
7,585,200 B1 * 9/2009 McLaren ..................... 450/89

OTHER PUBLICATIONS

Webpage; http://www.amazon.com/Single-Try-Absorbing-Comfortable-S-M-L-XL-XXL/dp/B002MHZo6Y/ref=pd_sbs_a_1; "Absorbing Comfortable White Bra Liner" (4 pages).
Webpage; http://www.amerimark.com/cgi-bin/amerimark/prod/22351/item_detail.html?keywords=bra%20liner&srcmode=&sortbyprice=; "Bra Liners" (1 page).

(Continued)

*Primary Examiner*—Gloria Hale
(74) *Attorney, Agent, or Firm*—Stetina Brunda Garred & Brucker

(57) ABSTRACT

A foldable one-piece insert worn between the bra and the body having irritation reducing and/or absorbent material portions which line the bra cup and that lie under the supported breast, and portions which extends toward the torso rear under the bra side straps and a portion extending below the bra line along the torso. The invention further includes a material tab disposed between the material portions lining the bra cups, which can optionally be worn up to bridge the area between the bra cups for added protection, comfort and absorption of perspiration, or be folded down and out of sight when worn with lower cut neckline outer garments.

17 Claims, 3 Drawing Sheets

OTHER PUBLICATIONS

Webpage; http://bramates.com/?gclid=CPu4j4LQiJ0CFRyenAod1ha7bg; "BraMates Bra Liners" (2 pages).

Webpage; http://www.comforthouse.com/bralin.html; "Absorbent Bra Liners Keep You Dry" (2 pages).

Webpage; http://www.amazon.com/3-Pack-Absorbing-Comfortable-Liners-Sizes/dp/B0023XCKAA; "3-Pack Absorbing n' Comfortable Bra Liners" (5 pages).

Webpage; www.pambras.com/3252.html; "What is Pambra's, The Original Bra Liner?" (2 pages).

* cited by examiner 175
153
100
154
152
158
153
175

175
153
152
154
100
153
175

COMFORT BRA LINER

CROSS-REFERENCE TO RELATED APPLICATIONS

This application is a Continuation in part Application of U.S. Non-Provisional Application Ser. No. 12/257,975 filed Oct. 24, 2008.

FIELD OF THE INVENTION

The present invention relates to bra liners, in particular to bra liners having a contoured profile to provide selective contact with the body when used with conventional bras.

BACKGROUND OF THE INVENTION

Wearers of bras experience sores, rashes, skin tags and irritation under the breast resulting from perspiration and skin-to-skin contact. Furthermore, conventional bra construction offers little to address this problem area, having a material or construction which are designed for esthetic concerns. Additional discomfort arises in areas under the bra peripherally related to the breast such as under the side straps, and in areas adjacent to the bra, such as immediately below the bra line along the torso.

SUMMARY OF THE INVENTION

The bra liner accordingly to the present invention provides a foldable one-piece insert worn between the bra and the body having irritation reducing or absorbent material portions which line the bra cup and that lie under the supported breast, and portions which extends toward the torso rear under the bra side straps, and a portion extending below the bra line along the torso.

A further feature includes a material tab disposed between the bra cup liners which can optionally be worn up to bridge the area between the bra cups for added protection, comfort and absorption of perspiration, or be folded down and out of sight when worn with lower cut neckline outer garments.

A still further feature according to the present invention provides removable inserts which are retained within the bra cup by material associated with the bra cup liner to help prevent dislocation of the inserts, which may comprise additional irritation reducing or absorbent material which may be desirable for comfort after surgery or exercise. Inserts also include appropriately shaped structures which provide lift, support, protection or esthetic enhancement.

A still further feature includes a curved front edge of the cup liner portions which are shaped to lie under the breast while avoiding contact with the breast nipple and areola areas to reduce of potential irritation to allow convenient breast feeding.

When worn, the bra liner according to one aspect of the present invention is foldable with one portion including the cup liners being placed in the bra cups, and a second portion which is unfolded and placed below the bra under the bra cups. Additional members extend from the cup liners and are placed between the bra straps and the wearer. The bra liner may be adjusted by the wearer to separate skin-to-skin contact and otherwise positioned between the bra and the torso for the desired comfort and/or absorption not possible with the bra. While worn, the material tab between the cup liners may be revealed by folding up, between the bra cups, or down, and inserts may be added or removed as desired.

BRIEF DESCRIPTION OF THE DRAWINGS

Various objects, features, and attendant advantages of the present invention will become more fully appreciated as the same become better understood when considered in conjunction with the accompanying drawings, in which like reference characters designate the same or similar part throughout the several view, and wherein.

DETAILED DESCRIPTION

Figure 1:
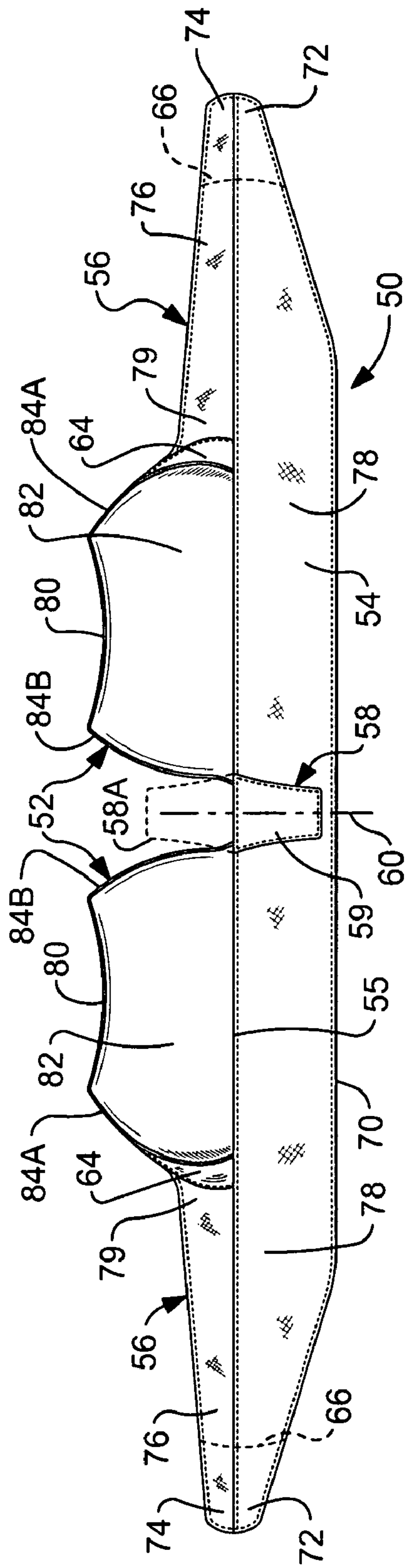
FIG. 1 is a rear elevation view of one embodiment of the present invention.
Figure 2:
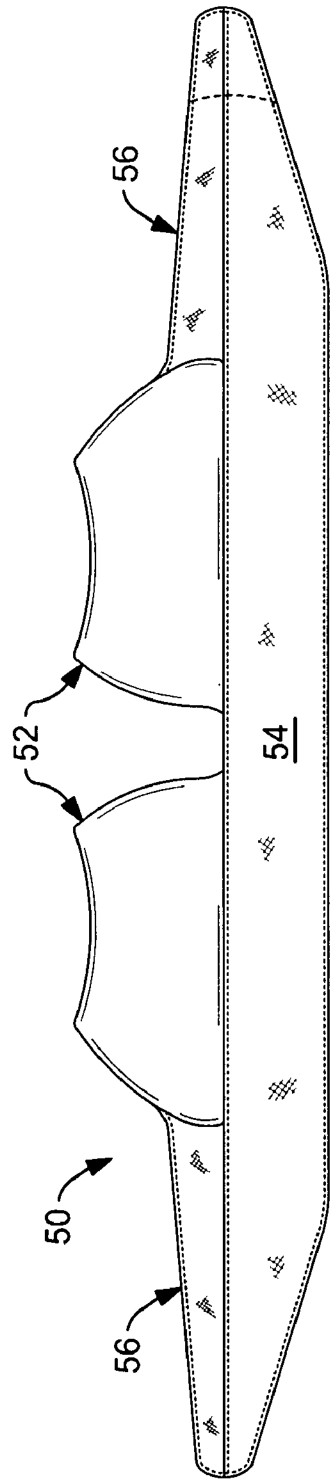
FIG. 2 is a front elevation view of the embodiment of FIG. 1.
Figure 3:
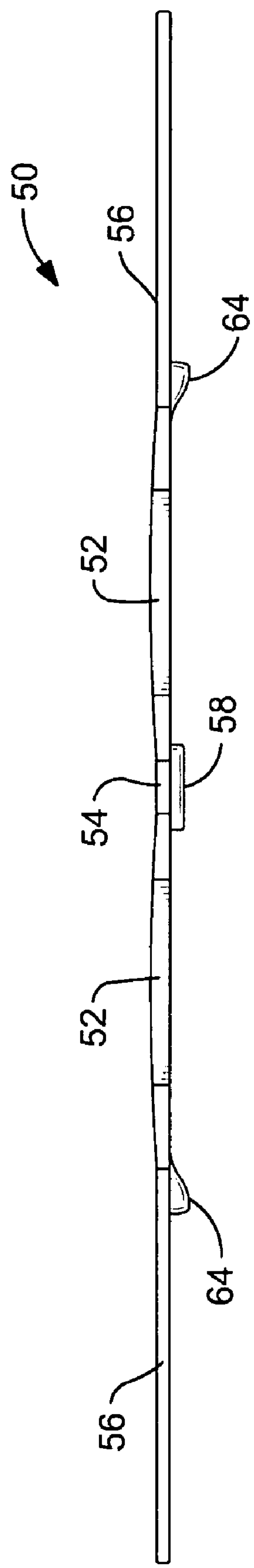
FIG. 3 is a plan view of the embodiment of FIG. 1.

With the construction of a typical bra being understood, an exemplary embodiment 50 according to the present invention is shown in FIGS. 1-3, including cup liners 52 which the wearer inserts into the bra and places under the breast, is attached to a strip 54 which retains the cup liners 52 in relative position and generally symmetrically outward from a midline 60, and when worn extends at least partially below the bra to be generally disposed over and at least partially in contact the body adjacent to the breast area to provide additional comfort and/or absorption in that area as well. The exemplary bra liner 50 further includes material bands 56 extending from the cup liner 52 parallel and include edges 76 connected to the edge 78 of strip 54 toward the ends thereof to form a foldable seam 55 with an opposing edge 70.

In the exemplary embodiment 50, both the bands 56 and the strip 54 have outer ends 74 and 72 respectively, terminating at substantially the same distance from the midline 60, but alternate embodiments may have either band(s) 56 or strip 54 extend farther. Typically, the bands 56 extend at least partially under the bra side straps (not shown) when in use. Furthermore, for applications where the bra liner 50 is to be worn to more completely encircle the body of the wearer, at least the bands 56 (and optionally the ends 72 of strip 54) can extended further along the bra straps to extend further around the torso of the wearer, and in some embodiments, touch or overlap each other. Alternately, embodiments having a shorter terminus 66 of the bands 56 and/or strip 54 may be provided.

The cup liners 52 typically each have an arcuate edge 80 substantially opposite the edge 82 which edge 82 joins the strip 54 at seam 55, and further that arcuate edge 80 is generally shorter than edge 82 comprising material shaped or sufficiently pliant to conform to the bra cup when worn by the wearer. The edges 80 and 82 are connected by outer side 84A and inner side 84B, which are shaped to conform to provide the desired function as described above. The outer sides 84A are typically connected to the inner ends 79 of bands 56. The specific dimensions of the cup liner width between edges 80 and 82, as well as the shape or radius of the arcuate edge 80 is scaled according to the size of the wearer and corresponding bra, and dimensioned to substantially avoid contact with the breast nipple and if desired, the areola as well when placed in the bra.

A material tab 58 as shown in FIG. 1, has an edge 59 connected to the strip 54 edge 78 and is foldable thereon from a ‘down’ position as shown overlaying the strip 54, to an ‘up’ position 58*a* where it at least partially overlaps the cup insert 52 inner edges 84B. In the exemplary embodiment shown, the cup inserts are separated with an intervening space between inner edges 84A, and the present embodiment bridges at least a portion of that space. The tab 58 may be pulled up (58A) for protection, absorption and comfort as needed.

Figure 4:
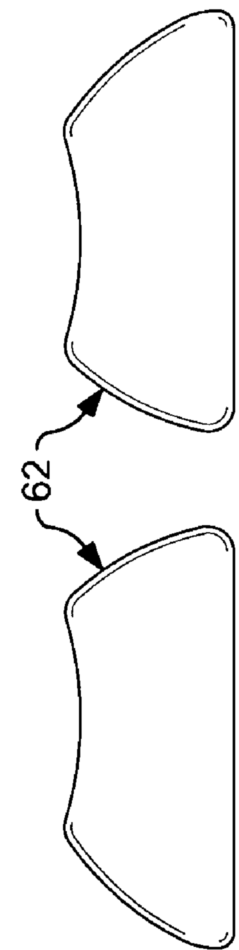
FIG. 4 is an elevation view of exemplary inserts as may be applied to the embodiment of FIG. 1.

Exemplary inserts 62, as shown in FIG. 4, may be applied to the present invention, and by reference to the exemplary embodiment 50 of FIGS. 1-3, generally retained on the cup liner 52 with optional flaps 64 shown in FIG. 1, which flaps 64 have outer edges connected to the cup liner outer edges 84A and lower edges connected to the cup liner 52 lower edge 82 to form a pouch to receive an edge, side, end, margin or other portion of the inserts 62 when worn by the wearer. The inserts are selected by the wearer to provide additional protection, to reduce irritation, to enhance absorption, to provide support, lift, and esthetic improvement (including prosthesis) as desired.

Figure 5:
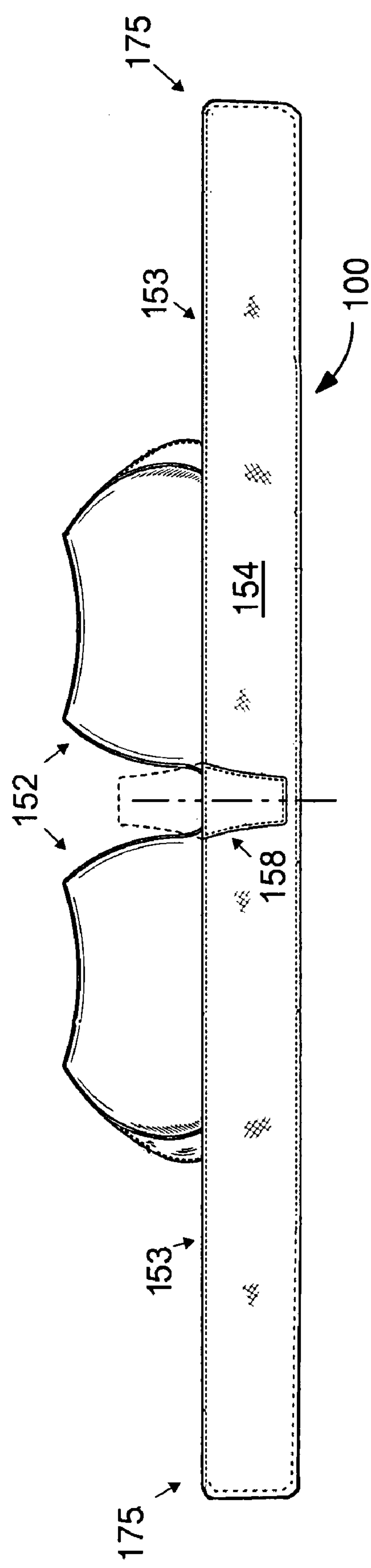
FIG. 5 is a rear elevation view of another embodiment of the present invention.
Figure 6:
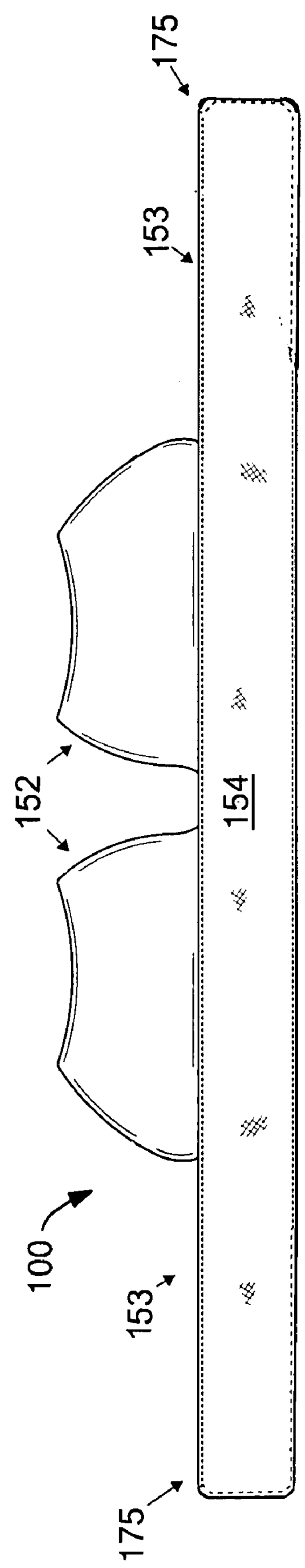
FIG. 6 is a front elevation view of the embodiment of FIG. 5.

A further embodiment 100 of the present invention is depicted in FIGS. 5 and 6. This alternative embodiment functions similarly to the embodiment portrayed in FIGS. 1-4, but does not include bands 56. Further, the bra liner 100 comprises round corners 175 at the termination of strip 154. In this embodiment, the cup liners 152 and tab 158 attach directly to the upper edge 153 of the strip 154.

The material used in the embodiments of the present invention in its entirety or individual component members thereof, may comprise irritation mitigating material, perspiration or fluid absorbent material, elastic material, padding, and other material sufficient to provide the embodiments described above. Particular material such as cotton, cotton blends and organic or non-allergenic material may be used for all or portions of the various embodiments of the present invention.

The embodiments according to the present invention may provide different sizing from small to extra large, and offer extended length to accommodate users who wish to extend the bra liner to farther under the bra side straps to extend to the back of the torso. Further embodiments are adapted for use with nursing bras that may be used in accordance with the opening afforded by the front edge of the cup liner portion. Further modifications and substitutions made by one skilled in the art are within the scope of the present invention which is not to be limited except by the claims which follow.

What is claimed is:

1. A bra liner for use under a bra, the bra having a strap with cups attached thereto for supporting breasts of a wearer, the liner comprising:

an elongate strip of thin absorbent material fittable under the strap of the bra, the strip having opposed end portions defining a length, upper and lower edge portions defining a width, the length of the strip being greater than the width of the strip;

a pair of cup liners fittable under the cups of the bra, the cup liners having a bottom edge portion attached to the upper edge portion of the strip, the pair of cup liners disposed substantially symmetrically on the upper edge portion of the strip, the cup liners having an arcuate concave top edge portion substantially opposite the bottom edge portion of the cup liners, the cup liners having opposed inner and outer edge portions extending between the bottom edge portions and top edge portion of the cup liners; and a tab having a bottom edge portion attached to the upper edge portion of the strip between the cup liners, the tab partially overlapping the inner edge portions of the cup liners, and the tab traversable between a folded position and an upright position, in the upright position, the tab bridging the cup liners, in the folded position, the tab being folded away from the cup liners and toward the strip.

2. The bra liner of claim 1, further comprising a pair of flaps each attached to the upper edge portion of the strip and to outer edge portions of the cup liners, the flaps and the cup liners forming a pocket.

3. The bra liner of claim 2, further comprising an insert at least partially insertable into the pocket, the insert being fabricated from an absorbent material.

4. The bra liner of claim 1, wherein at least one of said strip, cup liner, tab and flap comprises an absorbent material.

5. The bra liner of claim 1, wherein the cup liners define a width and a length, the width of the cup liner being less than the length of the cup liner.

6. The bra liner of claim 1, further including a foldable seam thereon.

7. A bra liner for a bra, the bra having a strap with cups attached thereto, the liner comprising:

a pair of cup liners fittable under the cups of the bra;

a strip finable under the strap of the bra, the strip having an upper edge portion, the pair of cup liners attached to the upper edge portion with a space therebetween; and a foldable tab connected to the strip, the tab traverseable between a folded position and an unfolded position, in the unfolded position, the tab overlays the space, in the folded position, the tab is folded toward the strip.

8. The bra liner of claim 7, further including:

an insert fabricated from an absorbent material, and retainer defining an outer periphery a portion of the outer periphery attached to the cup liner for forming a pocket which receives the insert.

9. The bra liner of claim 7, wherein the cup liner and strip are fabricated from fluid absorbent material or wicking material.

10. A bra liner for use between a bra and the wearer thereof wherein said bra includes at least one cup and at least one strap encircling the torso of said wearer, a position of the bra strap on the wearer's torso defining a bra line, the bra liner comprising:

a first cup liner disposable between said cup and the wearer;

a strip of thin material disposable at least partially under said strap with the first cup liner attached to the strip, a bottom portion of the strip extending below the strap.

11. The bra liner of claim 10, further including an insert retainer, a portion of an outer periphery of the insert retainer attached to the first cup liner for forming a pouch with the first cup liner.

12. The bra liner of claim 10, further including an absorbent insert disposed within said pouch formed by said insert retainer.

13. The bra liner of claim 10, wherein said strip comprises a strip having a length sufficient to encircle said torso.

14. The bra liner of claim 10, further comprising a second cup liner attached to said strip, and a tab attached to said strip, the tab traverseable between a folded position and an unfolded position, in the unfolded position, the tab disposed between the cup liners, in the folded position, the tab being folded away from the cup liners.

15. A bra liner for a bra, the bra having a strap and cups attached to the strap, the liner comprising:

an elongate strip of thin material having opposed end portions defining a length, opposed upper and lower edge portions defining a width, and a middle portion between the opposed end portions, the length of the strip being greater than the width of the strip;

a pair of cup liners having a bottom edge portion attached to the upper edge portion of the elongated strip, the cup liners disposed substantially symmetrically outward from said middle portion, said cup liners each having a bottom edge portion and an arcuate concave top edge portion substantially opposite said bottom edge portion, wherein top and bottom edge portions are each connected by opposing inner and outer edge portions and said inner edge portions of each said cup liner is proximal said middle portion, a pair of bands each having inner and outer end portions defining a length each said bands being attached to said strip upper edge portion; and a tab having a bottom edge portion joined to said strip upper edge portion, the tab partially overlapping said cup liner inner edge portions, the tab being traverseable between a folded position and an unfolded position, in the unfolded position, the tab is disposed between the cup liners, in the folded position, the tab is folded toward the strip.

16. The bra liner of claim 15, wherein at least one of said strip and said bands has a diminished width distal from said middle portion.

17. The bra liner of claim 15, wherein at least one of said strip, cup liner, tab and flap comprises an absorbent material.

* * * * *